(12) United States Patent
Kubota et al.

(10) Patent No.: US 6,251,868 B1
(45) Date of Patent: Jun. 26, 2001

(54) METHOD FOR TREATING A HUMAN IMMUNODEFICIENCY VIRUS INFECTION

(75) Inventors: Satoshi Kubota; Roger J. Pomerantz, both of Philadelphia, PA (US); Shigehisa Kitahara, Tokyo (JP)

(73) Assignees: Teijin Limited, Osaka (JP); Thomas Jefferson University, Philadelphia, PA (US)

( * ) Notice: Subject to any disclaimer, the term of this patent is extended or adjusted under 35 U.S.C. 154(b) by 0 days.

(21) Appl. No.: 09/069,809

(22) Filed: Apr. 30, 1998

(51) Int. Cl.⁷ .................................................. C07K 5/072
(52) U.S. Cl. ............................................. 514/19; 562/557
(58) Field of Search .................................. 514/19

(56) References Cited

U.S. PATENT DOCUMENTS

| | | | | |
|---|---|---|---|---|
| 4,927,808 | * | 5/1990 | Kitahara | 514/19 |
| 5,464,825 | * | 11/1995 | Anderson | 514/18 |
| 5,596,011 | * | 1/1997 | Repine | 514/369 |
| 5,607,974 | * | 3/1997 | Droge | 514/562 |
| 5,624,955 | * | 4/1997 | Nagasawa | 514/513 |
| 5,824,664 | * | 10/1998 | Schein | 514/143 |
| 5,843,785 | * | 12/1998 | Merzenberg | 436/86 |

FOREIGN PATENT DOCUMENTS

| | | |
|---|---|---|
| 276317 | 8/1988 | (EP) . |
| WO 92/21368 | 6/1997 | (WO) . |
| WO 97/21443 | 6/1997 | (WO) . |

OTHER PUBLICATIONS

Derwent Abstract of EP 736770A, 1996.*

* cited by examiner

Primary Examiner—F. T. Moezie
Assistant Examiner—David Lukton
(74) Attorney, Agent, or Firm—Sughrue, Mion, Zinn, Macpeak & Seas, PLLC

(57) ABSTRACT

The present invention provides a method for preventing or treating a human immunodeficiency virus (HIV) infection, including a new or an asymptomatic infection as well as AIDS, comprising administering to a mammal in need thereof a HIV infection preventing or treating effective amount of a γ-L-glutamnyl-L-cysteine ester compound of formula (I):

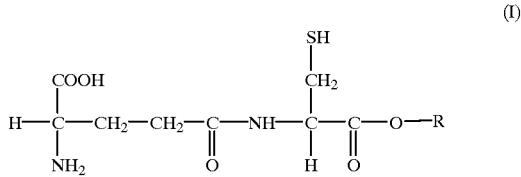

wherein R is a straight chain, branched or cyclic hydrocarbon group having 1–10 carbon atoms, or a straight chain or branched hydrocarbon group having 1–5 carbon atoms substituted with an aromatic group; or the oxidized dimer obtained by dehydrogenation between two γ-L-glutamyl-L-cysteine esters having formula (I).

10 Claims, 5 Drawing Sheets

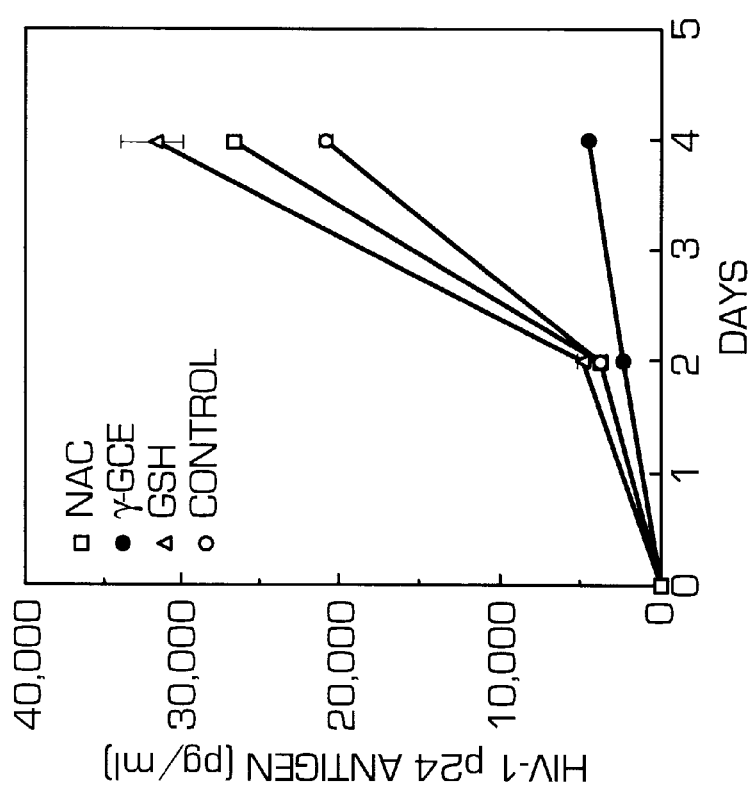
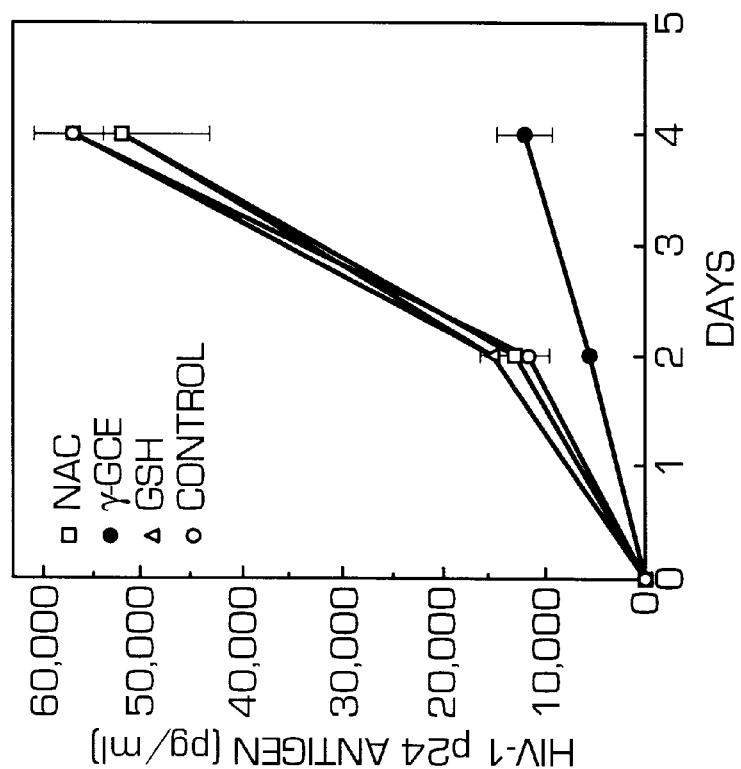

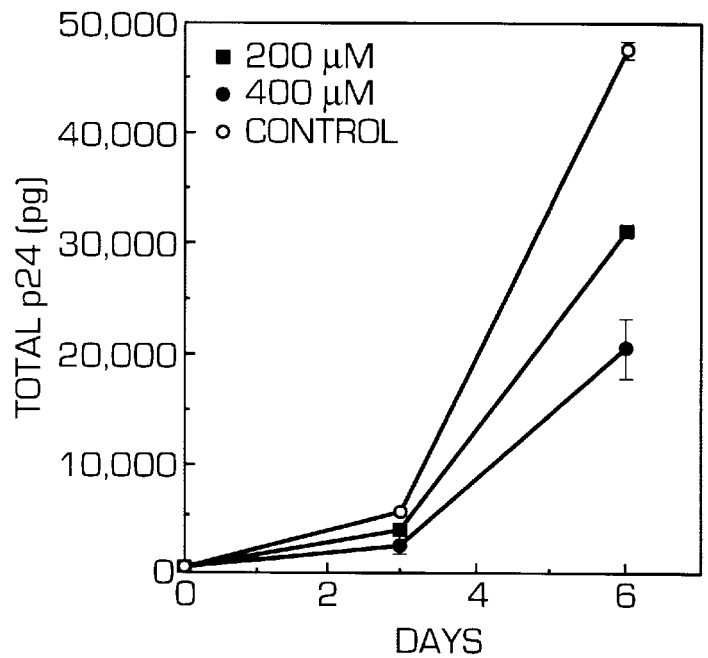
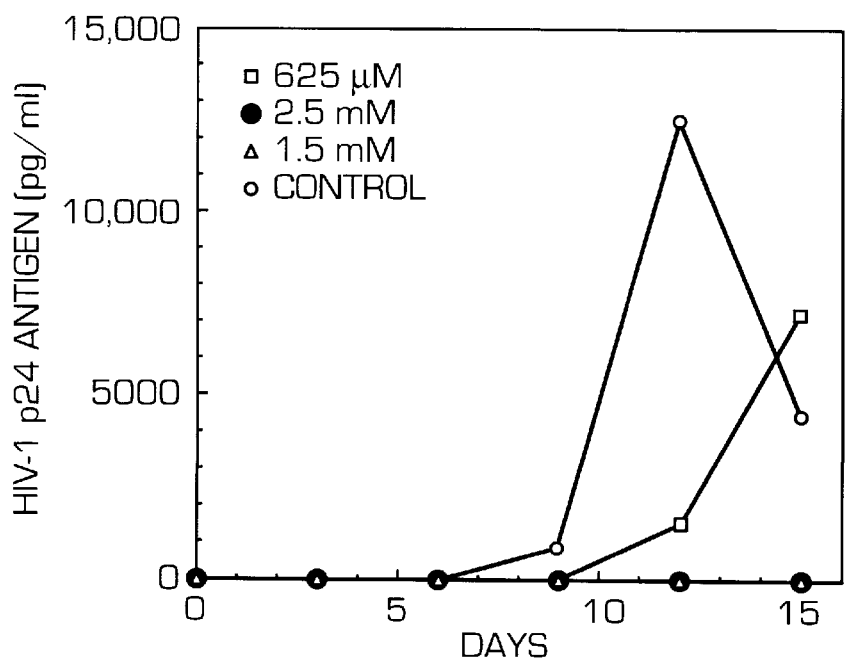

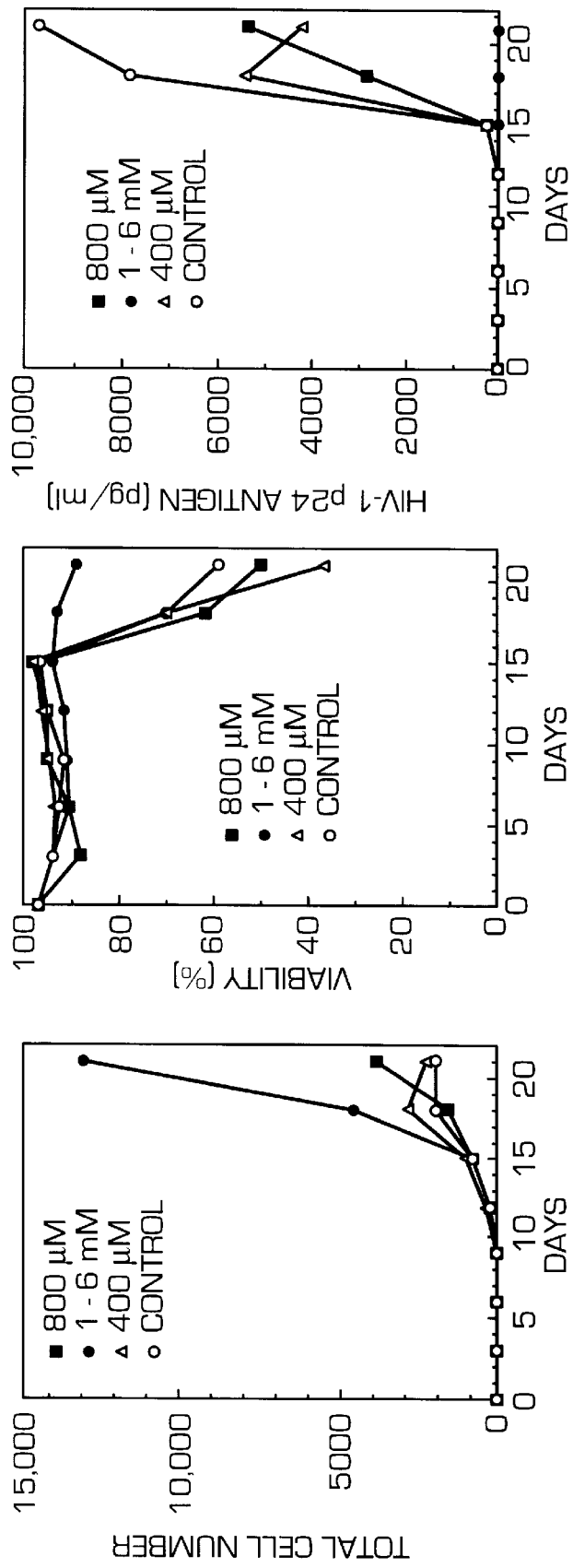

METHOD FOR TREATING A HUMAN IMMUNODEFICIENCY VIRUS INFECTION

TECHNICAL FIELD

The present invention relates to a method for preventing or treating a human immunodeficiency virus (HIV) infection, comprising administering to a mammal in need thereof a HIV infection preventing or treating effective amount of a γ-L-glutamyl-L-cysteine ester compound or an oxidized dimer obtained by dehydrogenation of two identical molecules of such.

BACKGROUND ART

The potential inhibitory effects of anti-oxidative agents, including glutathione (GSH) and its precursors, against human immunodeficiency virus type I (HIV-1), have been investigated over the last several years. In early studies, reducing compounds such as D-penicillamine, 2,3 dimercapto-1-propanol and N-acetylcysteine (NAC) were found to inhibit HIV-1 long terminal repeat (LTR)-directed viral gene transcription (FEBS Letters 1988; 236: 282–286, AIDS Res Human Retroviruses 1990; 7: 919–927, Proc Nati Acad Sci USA 1990; 87: 48844888, Proc Natl Acad Sci USA 1991; 88: 986–990). In parallel with these initial basic studies, reduction of GSH levels in plasma, peripheral blood cells, and lung epitheliallining fluid has been reported in HIV-1-infected-individuals (Biol Chem Hoppe-Seyler 1989; 370: 101–108, AIDS Res Human Retroviruses 1992; 2: 305–311, Lancet 1989; 11: 1294–1298). GSH is known not only as a major intracellular anti-oxidant, but also as an modulator of the immune system (J Immunol 1985; 135: 2740–2747). Hence, altering the GSH deficiency of HIV1-infected individuals by glutathione precursors has been hypothesized to be one of the rational therapeutic strategies to prevent HIV-1 propagation in vivo (AIDS Res Human Retroviruses 1992; 8: 209–215, Blood 1995; 86: 258–267, Blood 1996; 87: 4746–4753). In this manner, the inhibitory effects of GSH pro-drugs, such as NAC, against HIV-1 have been further characterized. These compounds have been shown to be capable of inhibiting HIV-1 gene transcription, which is induced by tumor necrosis factor alpha (TNF-α) or phorbol 12-myristate 13-acetate (PMA), from latent proviruses. This is a model for the cellular latent stage of HIV-1 infection (Proc Natl Acad Sci USA 1991; 88: 986–990, Cell 1990; 61: 1271–1276). Of note, in a recent report, enhancement of HIV-1 growth by NAC was described in peripheral blood mononuclear cells (PBMC) (AIDS 1997; 11: 33–41).

Recent studies have demonstrated that the replication of HIV-

I is continuously active in lymphoreticular tissues (Nature 1993; 362:355–358, Nature 1993; 312: 359–362). Therefore; it may be difficult to significantly alter HIV-1 infection only by keeping latent HIV-1 proviruses in a non-replicative state, without shutting off the massive virus production from so-called late-phase infected cells and subsequent further rounds of infection. It has been implied that, in order to slow down the progression of the acquired immune deficiency syndrome (AIDS), removal of the late-phase infected cells may be critical (Science 1996; 272: 1962). However, there has been no compounds which display a selective removal of HIV-1 itself and HIV-1-infected cells, although a vast number of anti-HIV-1 chemotherapeutic candidates have been described. Similarly, although there have been a various reports which described the anti-HIV-1 effects of a variety of anti-oxidants (FEBS Letters 1988; 236: 282–286, AIDS Res Human Retroviruses 1990; 7: 919–927, Proc Natl Acad Sci USA 1990; 87: 4884–4888, Proc Natl Acad Sci USA 1991; 88: 986–990), no such compound was reported to block acute HIV-1 infection.

The γ-L-glutamyl-L-cysteine ester compound of formula (I):

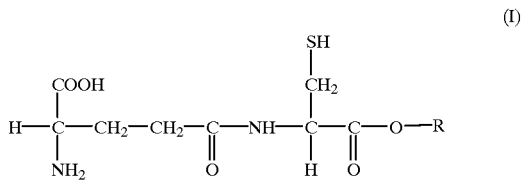

wherein R is a straight chain, branched or cyclic hydrocarbon group having 1–10 carbon atoms, or a straight chain or branched hydrocarbon group having 1–5 carbon atoms substituted with an aromatic group; or the oxidized dimer obtained by dehydrogenation between two γ-L-glutamyl-L-cysteine esters having formula (I), is known as an antioxidant, working either directly or as a unique GSH pro-drug, thereby performing preventive or therapeutic effects against liver disease, cataracts, kidney disease, heart and liver reperfusion injury, arrhythmia, and lung disease, such as asthma, caused by active oxygen and free radical injury (WO 88/00182 (→U.S. Pat. No. 4,927,808) and WO 92/18420 (→U.S. Pat. No. 5,631,234)). In particular, γ-L-glutamyl-L-cysteine ethyl ester (γGCE) has been reported to be effective against cataracts (Ophthalmic Res 1991; 23: 51–58), hepatic injury (Res Corn Chem Pathol Pharmacol 1993; 82: 49–64), heart and liver reperfusion injury (Brit J Pharmacol 1991; 104: 805–810, J Am Coll Cardiol 1994; 24: 1391–1397, Circulation Res 1994; 74: 806–816, and, Transplantation 1992:54: 414–418) and asthma (Am Rev Respir Dis 1992; 145: 561–565). Howvever, there is not a report on the effects of γ-L-glutamyl-L-cysteine ester compound against HIV infection.

DISCLOSURE OF THE INVENTION

The inventors of the present invention have examined the anti-HIV-1 effects of γ-GCE which represents the above-mentioned γ-L-glutamyl-L-cysteine ester compound in vitro, by using (1) a vigorously HIV-1-producing human T-lymphocytic cell-line, a model for a HIV-1 production from late-phase infected cells in chronic HIV infection and (2) a HIV-1-inoculated T-lymphocytic cells, a model for an acute HIV-1 infection, and have found (1) that γ-GCE displays a novel biphasic repressive effect on chronic HIV-1 infection, unlike other glutathione pro-drugs, or other reported anti-oxidants; that is, i) in high doses, up to a concentration of 2.5 mM, in which neither GSH nor other GSH precursors show inhibitory effects, γ-GCE potently inhibits the production of HIV-1 by a selective cytopathic effect against infected cells, while the viability and growth of uninfected cells are unaffected at the same concentrations, ii) at lower concentrations (200–400 μM), γ-GCE significantly represses the viral production from chronically HIV1-expressing cells without affecting their viability, and iii) the discrepancy of the thresholds of the toxic doses between infected and uninfected cells is more than ten-fold; and (2) that relatively high doses of γ-GCE, utilized in acute HIV-1 infection of T-lymphocytic cells, entirely blocked the propagation of HIV-1, and rescued the cells from HIV-1-induced cell death, and that γ-GCE at such concentrations was found to directly inhibit the infectivity of HIV-1 within four hours. Those findings indicate that γ-GCE possesses excellent properties as an anti-HIV agent; namely, it is capable of shutting-off all three critical factors in HIV propagation: it inactivates HIV-1 itself, blocks acute infection, represses virus production from infected cells, and kills HIV-1-producing cells selectively, which no other anti-HIV-1 chemotherapeutic agents have ever been attained.

Thus, based on the above-mentioned findings, the present invention relates to a method for preventing or treating a HIV infection, including a new or an asymptomatic infection as well as AIDS, comprising administering to a mammal in need thereof a HIV infection preventing or treating effective amount of a γ-L-glutamyl-L-cysteine ester compound of formula (I):

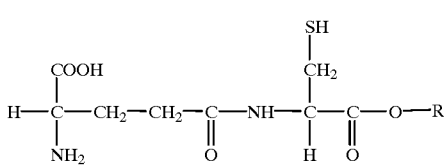

wherein R is a straight chain, branched or cyclic hydrocarbon group having 1–10 carbon atoms, or a straight chain or branched hydrocarbon group having 1–5 carbon atoms substituted with an aromatic group; or the oxidized dimer obtained by dehydrogenation between two γ-L-glutamyl-L-cysteine esters having formula (I).

BRIEF DESCRIPTION OF THE DRAWINGS

These results are the mean values of two independent experiments.

Panel B shows that 800 μM of γ-GCE (solid circles) dramatically impairs growth of chronically-infected highly HIV-1-expressing line, H-9/IIIB (H-9 cells infected with an HIV-1 strain, HIV-1IIIB), as compared with control (open circles); at the same time, it is observed that there are no significant cell growth after 12 days of treatment, and tfie cell viability also decreased below 40% (data not illustrated), suggesting γ-GCE's potent cytopathic effect against HIV-1 -producing cells.

Figure 2A:
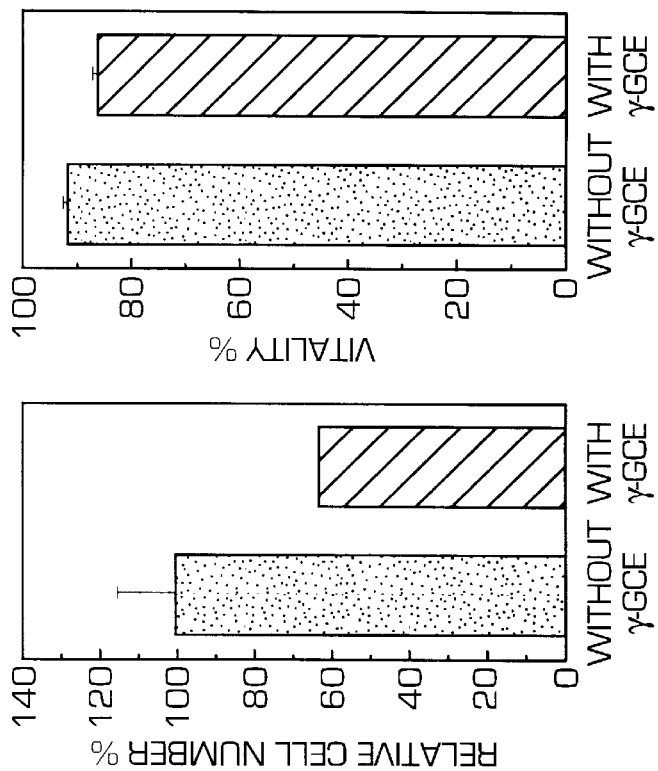
Figure 2B:
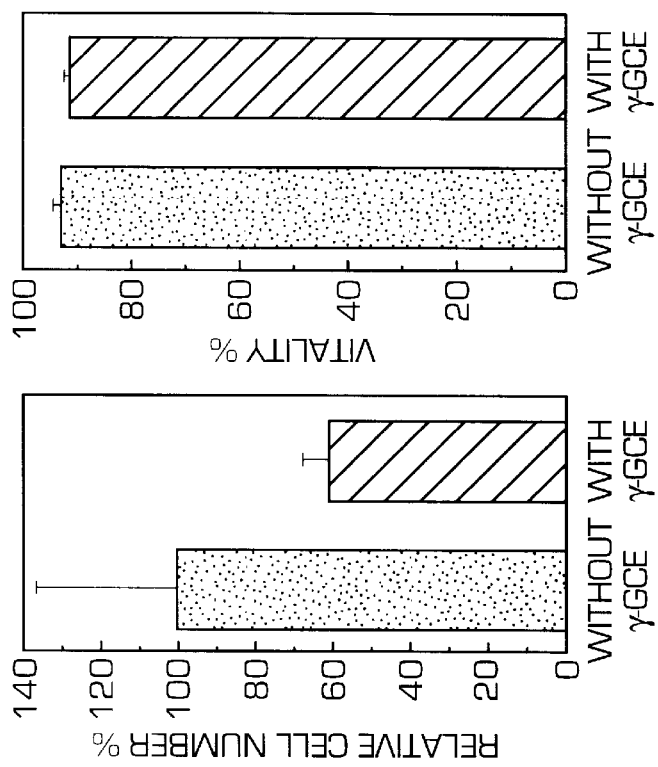

FIG. 2A shows that the cytotoxic effect of γ-GCE at 5 mM on uninfected H-9 cells in terms of viability and growth is approximately equivalent to that demonstrated in FIG. 2B for 400 μM on infected H-9/IIIB cells in terms of viability and growth, indicating that infected cells are approximately 12.5 times more sensitive to γ-GCE than uninfected cells, which represents a selective toxicity of γ-GCE for HIV-1-producing cells of H9 cells (rectangles: γ-GCE, diamonds: control).

FIG. 3A and 3B shows that at 1.25 mM, or 2.5 mM, respectively, γ-GCE (solid circles), which selectively decreases the viability of HIV-1-producing H-9 cells, almost completely shuts-off the logarithmic production of HIV-1 (as represented by p24 antigen) from H-9/IIIB cells, while neither GSH (triangles) nor NAC (rectangles) can overwhelm the vigorous HIV-1 production of H-9/IIIB at 1.25 mM FIG. 3A; rather they increases the virus production at 2.5 mM FIG. 3B, as compared with control (open circles), demonstrating a novel property of γ-GCE as an anti-HIV-1 agent.

FIG. 4 shows that 200 μM (solid rectangles), or 400 μM (solid circles) γ-GCE significantly inhibits the vigorous HIV-1 production (as represented by p24 antigen) of H-9/IIIB cells, without affecting the viability and growth of H-9/IIIB cells (as stated in Example 3), making a sharp contrast with the results of GSH or NAC in FIG. 3 in which they do not alter viral expression in higher concentrations, thus demonstrating the efficacy of γ-GCE as a GSH pro-drug against active and continuous HIV-1 production, even at low concentrations not toxic for infected cells.

FIG. 5C shows that 1.6 mM of γ-GCE (solid circles) completely blocks the propagation of HIV-1 (as represented by total HIV-1 p24 antigen), for 21 days postinfection, while in the presence of 400–800 μM γ-GCE (solid triangles and solid rectangles, respectively), acute infection was not inhibited significantly; and that the cells with 1.6 mM γ-GCE continues to grow actively, maintaining high viability, during the entire experiments, whereas the growth of control cells (open circles) with massive HIV-1 production demonstrated impaired cell growth FIG. 5A and cell death FIG. 5B.

FIG. 6 shows that pre-incubation with 2.5 mM (solid circles) and 1.25 mM (triangles) of γ-GCE for four hours completely inactivates HIV-1 directly, showing no onset of acute infection with these pretreated viruses in acute infection experiments, whereas pre-incubation of the virus with 625 μM of γ-GCE (rectangles) displayed only some delay of the onset in comparison with the control (open circles).

MODE OF OPERATION

In the above-mentioned formula (I), R represents a straight chain, branched or cyclical hydrocarbon group having 1–10 carbon atoms, or a straight chain or branched hydrocarbon group having 1–5 carbon atoms substituted with an aromatic group. In addition, the oxidized dimer refers to a dimer in which disulfide bond (—S—S—) is formed following dehydrogenation of two identical molecules of the above-mentioned formula (I).

The γ-L-glutamyl-L-cysteine ester compound indicated in the above-mentioned formula (I), or its oxidized dimer, can be manufactured according to the methods described in, for example, WO 88/00182 (→U.S. Pat. No. 4,927,808), Japanese Unexamined Patent Publication No. 64-19059 (→Japanese Patent No. 2569060) and Japanese Unexamined Patent Publication No. 64-26516 (→Japanese Examined Patent Publication No. 8–553090).

In the above-mentioned formula (I), specific examples of R include a methyl group, ethyl group, n-hexyl group, n-octyl group, isopropyl group, 2-methyl-2-propenyl group, cyclohexyl group and benzyl group. Although the compounds indicated in the above-mentioned formula (I) include all γ-L-glutamyl-L-cysteine ester compound in which a particular R group is bonded, typical examples of this compound include γ-L-glutamyl-L-cysteine ethyl ester.

In the case of using the γ-L-glutamyl-L-cysteine ester compound of the above-mentioned formula (I) or its oxidized dimer as a medical drug pertaining to the present invention, these compounds may be used in their free form or in the form of pharmacologically acceptable acidic or basic addition salts. When used in the form of a salt, the added acidic or basic groups may either be inorganic or organic compounds, and are not limited in any manner as long as they are sufficiently effective when used as a salt, and have no or low toxicity.

The compound of the above-mentioned formula (I) or its oxidized dimer may be administered orally, non-orally or via the respiratory tract in the desired form by mixing with pharmacologically acceptable carriers, vehicles, solvents, dilteiets, coloring agents, preservatives, neutralizers and stabilizers for prevention and treatment pertaining to the present invention.

Oral preparations can be either solid preparations such as tablets, granules, powders and capsules, or liquid preparations such as syrups, elixirs, emulsions and suspensions. In addition, non-oral preparations can be in the form of injection preparations, suppositories or external skin preparations. These preparations are made according to routine methods by adding pharmacologically acceptable adjuvants to the compound of the above-mentioned formula (I) or its oxidized dimer. Moreover, these preparations can also be made into the form of time-released preparations according to known methods.

Solid preparations for oral administration are made into powders by mixing the compound of the above-inentioned formula (I) or its oxidized dimer with a vehicle such as lactose, starch, cellulose crystal, methyl cellulose, glycerin, sodium alginate, gum arabic, calcium hydrogenphosphate, meta-magnesium aluminum silicate, calcium lactate, sodium chloride, calcium carbonate and kaolin, or, if necessary, made into granules by adding a disintegrating agent such as hydroxypropyl cellulose, polyvinyl pyrrolidone, saccharose, sodium alginate and sodium bicarbonate followed by granulation. Tablets are made by forming these powders and granules into tablets as is, or by adding a glossing agent such as talc or magnesium stearate. Moreover, the above-mentioned granules or tablets can be coated with a base such as methyl methacrylate copolymer or hydroxypropyl methyl cellulose phthalate to form an enteric coated preparation, or coated with ethyl cellulose or a hardened oil to form a time-release preparation. Capsules can be formed into hard capsules by filling with powder or granules, or formed into soft capsules by covering with a gelatin film after suspending or dissolving the compound of the above-mentioned general formula (I) or its oxidized dimer in glycerin, polyethylene glycol or olive oil and so on.

Liquid preparations for oral administration can be formed into a syrup by dissolving the compound of the above-mentioned formula (I) or its oxidized dimer in water with a sweetener such as glycerin or sorbitol, an elixir by adding ethanol or essence, or an emulsion or suspension by adding polysorbate 80, sodium carboxymethyl cellulose or gum arabic and so on.

Injection preparations are formed into single-dose or long or short-term continuous injection preparations for subcutaneous, intramuscular, intravenous or intraarterial injection by dissolving the compound of the above-mentioned formula (I) or its oxidized dimer in distilled water for injection together with a pH regulator such as disodium hydrogenphosphate, sodium dihydrogenphosphate, sodium hydroxide, hydrochloric acid, lactic acid or sodium lactate, an isotonic agent such as glucose or sodium chloride, and an SH group stabilizer such as sodium bistilfite, ascorbic acid or sodium ethylene diamine tetraacetate, and filling into ampules or polyethylene or glass containers following aseptic filtration. In addition, injection preparations of the type that are prepared as needed can be made by freeze-drying in a vacuum following the addition of dextrin, cyclodextrin, mannitol, gelatin and so on. In addition, the compound of the above-mentioned formula (I) or its oxidized-dimer may also be formed into an injection preparation contained in liposomes or microspheres in accordance with known methods.

Suppositories can be made by heating and melting the compound of the above-mentioned formula (I) or its oxidized dimer with polyethylene glycol, lanolin, mono-, di- or triglycerides of fatty acids or cocoa butter, and coating with gelatin, etc., after either cooling to plasticize, or suspending or dissolving in soy bean oil, polyethylene glycol and so on.

External skin preparations can be made by adding the compound of the above-mentioned formula (I) or its oxidized dimer to polyethylene glycol, white vaseline or liquid paraffin, etc., and may be in the form of an ointment, cream or gel and so on.

Preparations administered via the respiratory tract are administered in the form of fine granules of the compound of the above-mentioned formula (I) or its oxidized dimer using routine inhalation methods. It is desirable that the fine particles containing the drug as its effective component be in the form of an aerosol or powder, and have a particle size of 0.5–50 $\mu$m. Examples of devices that can be used to produce the aerosol include ultrasonic and jet spray type nebulizers, and sprayers using lower alkanes or fluorinated alkanes as the propellant. In addition, powders are administered using a simple inhaler coupled with spontaneous or forced inhalation.

Although there are no particular limitations on the concentration of the compound represented with formula (I) or its oxidized dimer in the present medical drug preparation, in general, 0.1–70% by weight, and preferably 1–50% by weight, is suitable for the concentration in the preparation. In addition, although there are also no limitations on its dosage, 0.01–5 g/day/patient, and preferably 0.1–2.5 g/day/patient, is suitable. With the exception of continuous injection, the number of administrations is normally 1–4 times per day.

EXAMPLES

Although the following provides a detailed explanation of the present invention using the Examples, the present invention is not limited by said Examples.

Example 1 Selective Cytotoxicity of γ-GCE for HIV-1-producing Cells

The uninfected human T-lymphoid cell-line, H-9, or H-9 cells infected with an HIV-1 strain, HIV-1IIIB (H-9/IIIB) (Science 1984; 224:497–500), were seeded in 24 or 96 well tissue culture plates at a density of 2–2.5×10$^5$/ml and maintained in RPMI-1640 tissue culture medium supplemented with 10% fetal bovine serum (FBS), with or without a variety of concentrations of γ-GCE, GSH, or NAC. Every two or three days, 50–80% of cell suspensions were removed, and the same amount of fresh medium, with the same concentrations of the compound to be analyzed were added for further incubation. At the same time-points, viable cells were counted for calculating the relative cell growth value, by the trypan-blue exclusion method. At the same time, cell viability was also monitored as the percentage of viable cells in the total cell population.

Figure 1B:
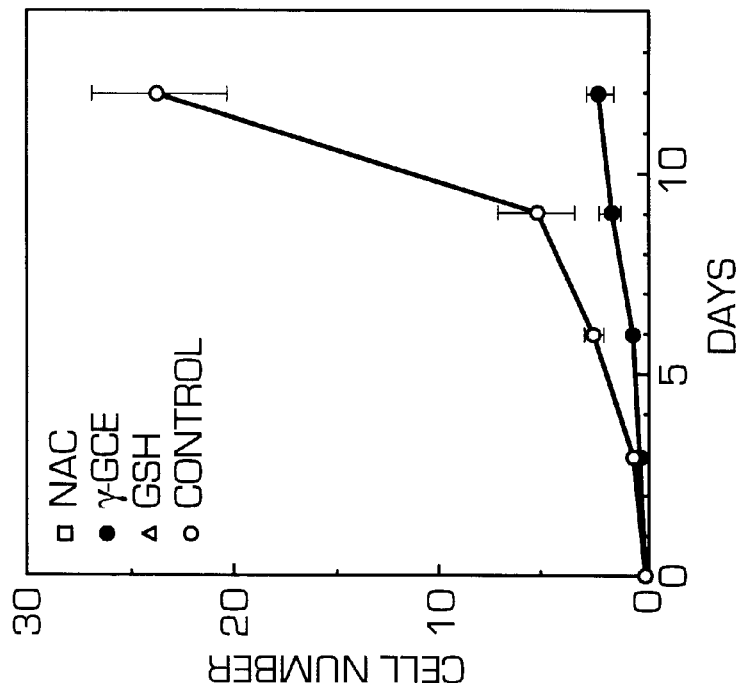
FIG. 1 panel A shows that 2.5 mM γ-GCE (solid circles), GSH (triangles) and NAC (rectangles) have no negative effects on growth of uninfected human T-lymphoid cell-line, H-9, as compared with control (open circles).
Figure 1A:
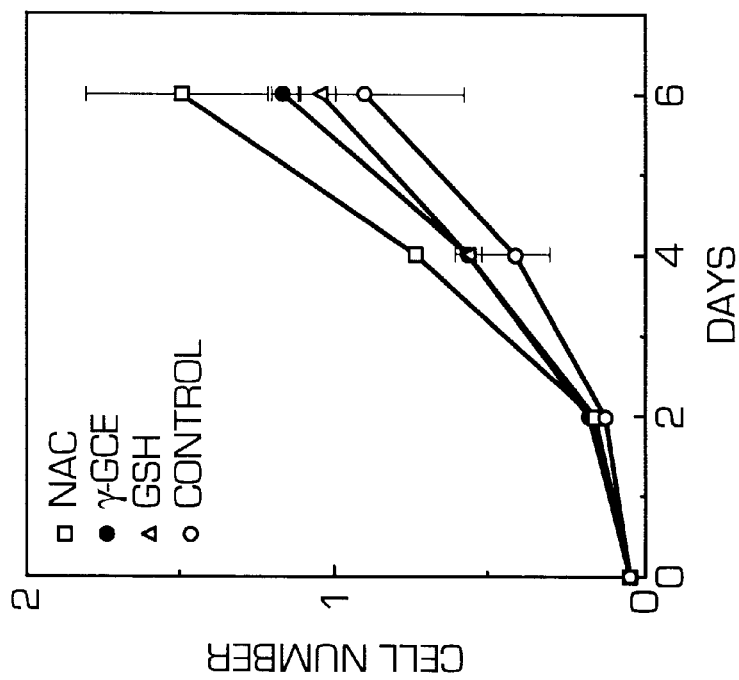

Initially, the effects of γ-GCE on the viability and cell growth of uninfected H-9 cells were evaluated, in comparison with GSH and NAC. At a concentration of 2.5 mM, γ-GCE demonstrated no negative effects on cell viability and growth (FIG. 1A). These results are quite similar to the findings with GSH, or NAC. Through 6 days of incubation, cell viability never decreased below 90% in any case, with the lowest value of 91.75±0.45% (NAC treated cells: Day 4), also suggesting γ-GCE's low toxicity on uninfected T-lymphocytic cells.

Subsequently, experiments which were similar to the above were carried out with a chronically-infected line, H-9/IIIB, which highly expresses HIV-1. In contrast to uninfected H-9 cells, surprisingly, H-9/IIIB cells displayed a remarkably high sensitivity to the cytotoxic effects of γ-GCE. As shown in FIG. 1B, at a concentration of γ-GCE as low as 800 μM, cell growth was dramatically impaired. On day six, the cell growth was reduced to a level of less than 40% of the control. Eventually after 12 days of treatment, no significant cell growth was observed. The cell viability also decreased below 40% after day 9 (data not illustrated), which suggests γ-GCE's relatively high cytotoxicity against HIV-1-producing cells.

To compare the cytotoxic effects of γ-GCE on H-9 and H-9/IIIB cells, a variety of concentrations of γ-GCE were tested to determine two doses for each cell-line, which gave equivalent cytotoxic profiles. It was observed that the cytotoxic effect of γ-GCE at 5 mM on H-9 cells was approximately equivalent to that demonstrated for 400 μM on H-9/IIIB cells (FIG. 2). Both cell-lines showed some decreases in relative cell growth, and minimal decreases in viability, after 6 days of γ-GCE treatment. In conclusion, H-9/IIIB cells are shown to be approximately 12.5 times more sensitive to γ-GCE than uninfected cells, which represents a selective toxicity of γ-GCE for HIV-1-producing cells.

Putting these results together, γ-GCE at a concentration between 800 μM to 2.5 mM was shown to be capable of altering the viability of H-9/IIIB cells, while not affecting uninfected H-9 cells.

Example 2 Potent Inhibition of HIV-1 Production by γ-GCE at Doses Which Selectively Impair the Growth and Viability of HIV1-producing H-9 Cells Following the discovery of a γ-GCE's differential cytotoxic effect in Example 1, the efficacy of such a selective toxicity for limiting HIV-1 production was evaluated.

H-9/IIIB cells were washed thoroughly with phosphate-buffered saline (PBS) and resuspended at a density of $1\times10^5$/ml in RPMI-1640/10% FBS with or without 1.25 or 2.5 mM of γ-GCE, GSH, or NAC. Since H-9/IIIB cells are constantly producing a large quantity of virus particles, stimulation with factors such as TNF-α or PMA were not required for carrying out these experiments. After two and four days, culture supernatant was removed, centrifuged to remove cells and debris, and evaluated by HIV-1 p24 antigen quantification. Measurement of the HIV-1 p24 antigen was performed by a sensitive enzyme-linked immunosorbant assay (ELISA) (DuPont).

Neither GSH nor NAC could overwhelm the vigorous HIV-1 production of H-9/IIIB. Rather they increased the virus production at 2.5 mM, which is in consistent with a previous report (AIDS 1997; 11: 3341). However, 1.25 or 2.5 MM γ-GCE almost completely shut-off the logarithmic production of HIV-1 from H-9/IIIB cells, apparently through a cytotoxic effect (FIG. 3). These data demonstrate a novel property of γ-GCE as an anti-HIV-1 agent.

Example 3 Significant Repression of HIV-1 Production by γ-GCE at Doses Which Do Not Affect the Viability of HIV-1-producing H-9 Cells Since γ-GCE is a potential anti-oxidant, inhibition of HIV-1-LTR-directed transcription within a non-toxic range of γ-GCE was also predicted. However, it was also presumed that it may be difficult for this type of compound to inhibit such constant and high retroviral production.

H-9/IIIB cells were washed with PBS and seeded at a density of $2\times10^5$/ml in RPMI-1640/10% FBS with or without 0.2or 0.4 mM of γ-GCE. Three and six days after initiation of experiments, culture supernatants were sampled and assayed, as described above. On day three, 72% of each cell suspension was removed, and fresh medium with a corresponding GSH pro-drug was added. Total HIV-1 p24 antigen production values on day six were deduced by multiplying raw values, on day six, with the dilution factor on day three.

Treatment of H-9/IIIB cells with low concentrations of γ-GCE is illustrated in FIG. 4. As expected, γ-GCE significantly inhibited the vigorous HIV-1 production of H-9/IIIB cells at low concentrations (200 μM and 400 μM), whereas higher concentrations of GSH or NAC did not alter viral expression (FIG. 3). With such γ-GCE treatment, cell viability was not significantly affected at either dose (>86%). Slower cell growth was observed only at 400 μM (as illustrated in FIG. 2B), but not at 200 μM (data not illustrated). These findings demonstrate the efficacy of γ-GCE as a GSH pro-drug against active and continuous HIV-1 production, even at low concentrations.

Example 4 Inhibition of Acute HIV-1 Infection by γ-GCE

If γ-GCE is able to remove HIV-1-producing cells effectively, it is expected to prevent HIV-1 from spreading over the entire population of cells during acute infection. To verify this hypothesis, an acute infection study was carried out.

For those experiments, an HIV-1 strain, NL-4-3 (J. Virol. 1986; 59: 284–291), was prepared, rather than using the HIV-1IIIB isolate (Science 1984; 224: 497–500) which lacks certain viral accessory genes and their translational products, some of which have been demonstrated to alter the early phase of infection.

Virus stocks of the HIV-1NL4-3 strain were prepared and titered as described previously (Hum Gene Ther 1995; 6: 1561–1571). H-9 cells ($3\times10^5$ cells.) were suspended in 1 ml of growth medium with or without γ-GCE at a variety of concentrations, and seeded in a chamber of a 24-well tissue culture plate. Virus suspension containing 30 pg of HIV-1 p24 antigen was added to each chamber, for the initial infection. Infection was carried out overnight at 37° C., then the cells were washed once with PBS, and once more with growth medium. The supernatant of the final wash was saved as a day 0 time-point. Washed cells were resuspended with corresponding media for further incubation at 37° C. Once in three days, cell suspensions and supernatants were harvested for cell counting and HIV-1 p24 antigen quantification. Measurement of cell growth, viability, and virus production were performed as described in a previous subsection. On the days of harvest, 200 μl of cell suspension was left in each well, and 800 μl of fresh medium with corresponding concentrations of γ-GCE was added to support cell growth, except day 18, on which 400 μl of cell suspension was left and 600 μl of medium was added to each well. Cell numbers at each time-point were determined accordingly, based on the accumulation of dilution factors along with the frequency of passage.

Infection of H-9 cells triggered a burst of virus production on days 12–15 post-infection, without γ-GCE. While in the presence of 400–800 μM γ-GCE, acute infection was not inhibited significantly, but 1.6 mM of γ-GCE completely blocked the propagation of HIV-1, for 21 days postinfection (FIG. 5, panel C). During the entire experiments, the cells with 1.6 mM γ-GCE continued to grow actively, maintaining high viability, whereas the growth of control cells with massive HIV-1 production demonstrated impaired cell growth (FIG. 5, panel A) and cell death (FIG. 5, panel B). Syncytia-formation was evident in all the control cell cultures with active production of HIV-1, by day 15 and at later time-points. With 1.6 mM of γ-GCE, syncytia-formation was not significantly observed in the cultures (data not illustrated).

Example 5 Direct Inactivation of HIV-1 by γ-GCE

The results of the acute HIV-1 infection study raised another possibility, that γ-GCE may inactivate the infectivity of HIV-1 before/along the infection process. For the examination of such a disinfecting effect of γ-GCE, we designed and carried out another series of experiments.

An HIV-1 virus stock (NL4-3) containing 6 ng of HIV-1 p24 antigen was pre-incubated in the presence or absence of γ-GCE in 20 ml of RPMI-1640/10% FBS for 4 hr at 37° C. Afterwards, acute infection of H9 cells were carried out, using 10 ml of each pretreated virus suspension into 1 ml of the cell suspension without γ-GCE, as described in the previous subsection. Sampling and maintenance of cell culture were also performed, following the same procedure as described in the previous subsection, without adding any γ-GCE through passage.

Surprisingly, γ-GCE treatment at 1.25 mM, or 2.5 mM for 4 hours caused the loss of infectivity of HIV-1, giving no viral production even after 15 days post-infection. Even at the lowest concentration (625 μM), γ-GCE caused some delay for the propagation of HIV-1 in H-9 cells. However, pre-incubation with the same concentrations of γ-GCE for one hour did not show significant interference with viral infectivity (data not illustrated). These data indicate the direct inactivation effect of γ-GCE against HIV-1 particles, and may be involved in the inhibitory effect observed in the HIV-1 acute infection experiments.

What is claimed is:

1. A method for killing human immunodeficiency virus (HIV)-infected T-lymphocytes or inactivating infectious HIV particles consisting of administering to a mammal infected with HIV a therapeutically effective amount of γ-L-glutamyl-L-cysteine ester of formula I

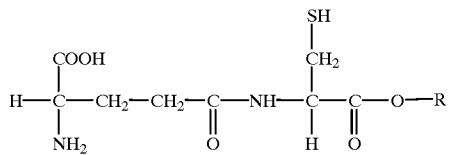

(I)

for a time and under conditions effective to kill HIV-infected T-lymphocytes or inactivate infectious HIV particles; wherein R is a straight chain, branched or cyclic hydrocarbon group having 1–10 carbon atoms, or a straight chain or branched hydrocarbon group having 1–5 carbon atoms substituted with an aromatic group; or the oxidized dimer obtained by dehydrogenation between two γ-L-glutamyl-L-cysteine esters having formula (I).

2. The method of claim 1, wherein R is an alkyl group having 1–10 carbon atoms.

3. The method of claim 1, wherein R is an ethyl group.

4. The method of claim 1, wherein said effective amount of said compound or said dimer is between 0.01–5 g/day.

5. The method of claim 1, wherein said effective amount of said compound or said dimer is between 0.01–2.5 g/day.

6. The method of claim 1, wherein said mammal is a human.

7. The method of claim 1, wherein said mammal is afflicted with a new HIV infection.

8. The method of claim 1, wherein said mammal is afflicted with an asymptomatic HIV infection.

9. A method for inactivating human immunodeficiency virus (HIV) comprising exposing the virus to γ-Glu-Cys-OEt for a time and under conditions effective to inactivate the HIV.

10. A method of inhibiting propagation of human immunodeficiency virus (HIV) in a mammal infected with HIV consisting of administering to said mammal a therapeutically effective amount of γ-L-glutamyl-L-cysteine ester of formula I

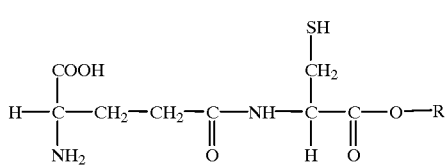

(I)

for a time and under conditions effective to inhibit propagation of HIV, wherein R is a straight chain, branched or cyclic hydrocarbon group having 1–10 carbon atoms, or a straight chain or branched hydrocarbon group having 1–5 carbon atoms substituted with an aromatic group; or the oxidized dimer obtained by dehydrogenation between two γ-L-glutamyl-L-cysteine esters having formula I.

* * * * *